United States Patent [19]

Marko et al.

[11] Patent Number: 4,774,347

[45] Date of Patent: Sep. 27, 1988

[54] REMOVAL OF CHLORINATED HYDROCARBONS FROM ALKYLSILANES

[75] Inventors: Ollie W. Marko; Robert D. Steinmeyer, both of Carrollton, Ky.

[73] Assignee: Dow Corning Corporation, Midland, Mich.

[21] Appl. No.: 161,705

[22] Filed: Feb. 29, 1988

[51] Int. Cl.$^4$ ............................................. C07F 7/20
[52] U.S. Cl. .................................................. 556/466
[58] Field of Search ........................................ 556/466

[56] References Cited

U.S. PATENT DOCUMENTS

| | | | |
|---|---|---|---|
| 3,151,045 | 9/1964 | Wrabotz et al. | 532/466 X |
| 4,127,598 | 11/1978 | McEntee | 556/466 X |
| 4,629,801 | 12/1986 | Soula et al. | 556/466 |

FOREIGN PATENT DOCUMENTS

| | | | |
|---|---|---|---|
| 50-39649 | 12/1975 | Japan | 556/466 UX |
| 59-233780 | 8/1984 | Japan | 556/466 |

OTHER PUBLICATIONS

Sommer et al., *J. Am. Chem. Soc.*, 69 (1947) p. 2108.

*Primary Examiner*—Paul F. Shaver
*Attorney, Agent, or Firm*—Carl A. Yorimoto

[57] ABSTRACT

A process for reducing the chlorocarbon content of alkylsilanes is described. The process comprises (A) contacting crude alkylsilanes, containing as a minor portion chlorocarbons, and a hydrogen-containing silane with a catalyst; wherein the catalyst is a sufficient amount of an effective Lewis acid forming material; (B) facilitating the reaction of the chlorocarbons with the hydrogen-containing silane in contact with the catalyst to convert the chlorocarbons to a linear or branched alkanes; (C) separating catalyst from the alkylsilanes and alkanes; and (D) recovering alkylsilanes with lowered chlorocarbon content.

14 Claims, No Drawings

REMOVAL OF CHLORINATED HYDROCARBONS FROM ALKYLSILANES

BACKGROUND OF THE INVENTION

This invention relates to the purification of organosilanes. More specifically, this invention relates to a means for chemically converting chlorinated hydrocarbon (chlorocarbon) impurities in alkylsilanes and isolating and recovering the purified alkylsilane.

High-purity alkylsilanes are needed for the ever-increasing quality needs of the industrial manufacture of organosilanes and organopolysiloxanes. In the preparation of alkylsilanes via the direct reaction of an alkyl halide with silicon, the crude alkylsilane mixture contains minor amounts of the whole spectrum of olefinic and chlorinated hydrocarbons. These materials in many cases cause separation problems with the commonly used practice of isolating by distillation the desired alkylsilanes contained in the crude product of the direct reaction, having boiling points very close to the various alkylsilanes. As impurities in the isolated alkylsilanes, these olefinic and chlorinated hydrocarbons pose serious quality problems.

Olefins are known to cause color problems in the preparation of organosilane and polyorganosiloxane intermediates and products. Chlorocarbons create a problem due to their thermal instability, potentially decomposing into an olefin and hydrogen chloride. As an example, an organohalosilane containing low levels of a chlorocarbon can be converted to a polyorganosiloxane with the chlorocarbon surviving early process steps, only to decompose causing an acidity problem with a later intermediate or product and also color problems due to the olefin formed.

Sommer et al., *J. Am. Chem. Soc.*, 69(1947) pp. 2108–2110, discloses that alkyl halides and trialkylsilanes in the presence of aluminum chloride interchange their halogen and chlorine atoms. Nowhere does Sommer et al. disclose use of this reaction as part of a process for the purification of alkylsilanes.

Motomiya, Japanese patent publication No. 50-39649, published Dec. 18, 1975, discloses a method for purification of organohalosilanes in which a Lewis acid or a metal hydroxide is used to convert unsaturated and saturated hydrocarbon impurities to polymers, facilitating recovery of purified organohalosilanes. Motomiya demonstrates that the presence of a hydrogen-containing silane compound is not necessary for the conversion of the hydrocarbons to a polymer to proceed. No mention is made of the conversion of chlorocarbons to saturated hydrocarbons.

Clay et al., Japanese Patent Publication No. 59-137312, published Aug. 7, 1984, discloses a method for purification of chlorosilanes in which chlorohydrides of elements from Group III or IV of the Periodic Table are contacted with chlorine to convert these chlorohydrides to chlorides to facilitate separation of these impurities from the desired chlorosilanes via distillation. No mention is made of applying this method to the removal of chlorocarbons from alkylsilanes.

SUMMARY OF THE INVENTION

It is an objective of the instant invention to provide a simpler means for isolating and removing chlorocarbon impurities from alkylsilanes than the present use of distillation.

The art includes chemistry describing the reaction of chlorocarbons with hydrogen-containing silane materials. However, nowhere in the art is it indicated that this chemistry can be applied to an industrial process for the purification of alkylsilanes.

The instant invention provides a process which converts a chlorocarbon impurity in an alkylsilane stream to saturated hydrocarbons and more highly chlorinated alkylsilanes. The alkylsilane stream, so treated, can be used directly without the quality concern created by the presence chlorocarbons. Additionally a mixture of alkylsilanes freed of chlorocarbons can more readily be processed by such conventional means as distillation.

DESCRIPTION OF THE INVENTION

In accordance with the instant invention there is provided a process for minimizing the chlorocarbon content of alkylsilanes under conditions that will be delineated herein. What is described, therefore, is a process for purifying alkylsilanes to lower the content of chlorocarbon impurities, wherein said alkylsilanes have the formula, $$R^i_a SiX_{4-a}$$

wherein each $R^i$ is independently selected from hydrogen atoms and alkyl groups containing 1, 2, 3, 4, 5, or 6 carbon atoms; X is a halogen atom; and wherein a has a value of 1, 2, 3, or 4, said process comprising (A) contacting crude alkylsilanes and a hydrogen-containing silane with a catalyst; wherein said crude alkylsilanes are a mixture which comprises as a major portion the alkylsilanes and as a minor portion the chlorocarbons; said chlorocarbons are selected from a group consisting of linear and branched alkylchlorides containing 3 or more carbon atoms and one or more chlorine atoms; said hydrogen-containing silane having the formula, $$R^{ii}_m H_n SiX_p,$$

wherein each $R^{ii}$ is independently selected from alkyl groups containing 1, 2, 3, 4, 5, or 6 carbon atoms; X is defined above; m has a value of 0, 1, 2, or 3; n has a value of 1 or 2; p has a value of 0, 1, 2, or 3; and the sum of (m+n+p) must equal 4;

and said catalyst is an effective Lewis acid forming material;

(B) facilitating reaction of the chlorocarbons with the hydrogen-containing silane in contact with the catalyst to convert the chlorocarbons to linear or branched alkanes;

(C) separating the catalyst from the alkylsilanes and alkanes; and (D) recovering alkylsilanes with lowered chlorocarbon content.

For the purposes of the instant invention the term "effective Lewis acid forming material" means that the catalysts that have been found effective in facilitating the reaction of a chlorocarbon with a hydrogen-containing material to form saturated hydrocarbons (alkanes) have all been Lewis acid forming materials. However, under certain conditions of the instant invention some Lewis acid forming materials, such as $ZnCl_2$, $CrCl_2$, and $NiCl_2$, are ineffective in comparison to other Lewis acid catalysts under the same conditions. It is recognized by the inventors that due to differences in physical characteristics and solubilities of the metal chlorides, the above may not follow the classic order of Lewis acid strengths. It is theorized that Lewis acid forming materials are generally effective as catalysts. However, this theory is not presented to limit the claims delineated herein. The preferred, most effective Lewis acid forming materials can be selected from a group consisting of alumina, silica-alumina mixtures, zeolites, aluminum chloride, cobalt chloride, ferric chloride, copper chloride, stannous chloride, palladium chloride, and zirconium chloride. Zeolites are such materials as silicoaluminates, also known as molecular sieves. The preferred catalysts are aluminum chloride, cobalt chloride, zirconium chloride, alumina, and silica-alumina mixtures. The preferred catalysts have demonstrated conversions of chlorocarbons greater than about 90 percent. The catalyst contacts the alkylsilanes and chlorocarbons as a solid. As such the catalyst can be in a form, for example, such as powders, granules, pellets, or lumps.

It is recognized by the inventors that, in addition to the reaction of chlorocarbons with hydrogen-containing silanes to form alkanes and more highly halogenated alkylsilanes, some of the more highly alkylated silanes, such as tetramethylsilane, may be consumed. The inventors believe that the catalyst of the instant invention causes some rearrangement of the more highly alkylated silanes with the other alkylhalosilanes and with dissolved hydrogen halide as well. This rearrangement is not detrimental to the benefits derived from the instant invention.

The alkylsilanes which are purified by the instant invention can be, for example, methylchlorosilane, methyldichlorosilane, dimethylchlorosilane, ethylibromosilane, n-butylfluorosilane, methyltrichlorosilane, dimethyldichlorosilane, trimethylchlorosilane, ethyltribromosilane, n-propyltrichlorosilane, ethylmethyldichlorosilane, t-butyldimethylchlorosilane, tetramethylsilane, tetraethylsilane, or mixtures thereof.

The chlorocarbon materials which are converted to alkanes can be, for example, 2-chloropropane, 1-chlorobutane, 2-chlorobutane, 2-chloro-2-methylpropane, 1-chloropentane, 2-chloropentane, 2-chloro-2-methylbutane, 1-chlorohexane, 2-chlorohexane, 3-chlorohexane, 3-chloro-2-methylpentane, 2-chloro-2,3-dimethylbutane, 3-chlorooctane or 2-chlorodecane. The inventors believe that methyl chloride and ethyl chloride are essentially unreactive under the conditions of the instant invention. The chlorocarbons are a minor portion of crude alkylsilane mixtures. As such, the chlorocarbon content at which the instant invention is effective can be as low as 10 parts per million (ppm), based upon the weight of the crude alkylsilanes. The chlorocarbon content of the crude alkylsilanes can be in a range from about 10 ppm to about 2 percent, based upon the weight of the crude alkylsilanes.

The hydrogen-containing silane used to effect conversion of the chlorocarbons to alkanes can be, for example, dichlorosilane, dimethylsilane, diethylsilane, methylchlorosilane, n-propylbromosilane, methyldichlorosilane, ethyldichlorosilane, dimethylchlorosilane, t-butylmethylchlorosilane, or trimethylsilane. The hydrogen-containing silane is normally a minor portion of the crude alkylsilanes. However, to assure that a sufficient quantity of the hydrogen-containing silane is present to maximize the conversion of the chlorocarbons to saturated hydrocarbons, a hydrogen-containing silane may be added to the crude alkylsilanes. Further, it is preferred that the hydrogen-containing silane should be present in the reaction mixture at a concentration at which the molar concentration of hydrogen atoms attached to silicon is in a stoichiometric excess relative to the chlorocarbon impurities. The stoichiometric excess affects the contact time necessary to convert the chlorocarbons and the degree of conversion. It is understood that less than the stoichiometric quantity of the hydrogen-containing silane may be utilized with the expected lower conversion of chlorocarbons to saturated hydrocarbons.

Contacting the catalyst with the crude alkylsilanes can be effected in either a batch or continuous mode. In a batch mode, liquid reactants and a solid catalyst can be contacted by such conventional means such as a stirred tank reactor. Contacting the reactants and solid catalyst can be effected in a continuous mode by such conventional means as a packed bed reactor or a stirred tank reactor with continuous feed and continuous product take-off. Contact of the crude alkylsilanes and the hydrogen-containing silane with the catalyst in a packed bed in a continuous mode is a preferred embodiment.

"Facilitating reaction of the chlorocarbons with the hydrogen-containing silanes in contact with the catalyst" means, for the purposes of the instant invention, providing such facilities as feed systems for the crude alkylsilanes and additional hydrogen-containing silanes; adequate agitation to assure sufficient contact of the liquid reactants with the solid catalyst in a stirred tank reactor; facilities for temperature control, such as a heat transfer system and automatic temperature control; and provisions for control of system pressure.

Catalyst concentration relative to the alkylsilanes and the hydrogen-containing silane is not critical to the operation of the instant invention. However, catalyst concentration will affect time for reaction completion and the degree of completion. Thus, a packed column in which the reactants contact a large amount of catalyst in a short period of time is preferred.

The reaction of the chlorocarbons with hydrogen-containing silanes is very rapid. The results of the examples, infra, indicate that the reaction proceeds at temperatures as low as ambient or 25° C. The inventors believe that temperatures of less than 150° C. can be utilized without significant thermal degradation of reactants and products. The inventors further believe that the reaction can occur in either the liquid phase or the vapor phase. However, it is preferred that the reactants be kept in liquid phase. Therefore, it is preferred to maintain the temperature in a range from about 25° to 100° C. to minimize reaction time. A pressure above atmospheric pressure is preferred to maintain the reactants as a liquid in this temperature range. It is more preferred to maintain a pressure in the range from about 40 to 80 pounds per square inch, gauge (psig) to allow utilization of standard processing equipment.

The reaction of the chlorocarbons and the hydrogen-containing silanes can be completed in a matter of minutes. To assure completion of reaction, it is preferred that the crude alkylsilanes, the hydrogen-containing silane, and the catalyst be in contact for greater than about one minute. In a packed column configuration, contact times of one minute or less have been shown to effect significant conversion of chlorocarbons. Preferred contact time is in a range from about 1 to 20 minutes.

Separating residual catalyst solids from the alkylsilanes and alkanes can be effected by conventional means. When the process is operated in a batch mode or a continuous mode in a stirred tank reactor, the total catalyst charge can be separated by such means as a settling tank, filtration, or a combination thereof. When a packed bed of catalyst is used in a continuous mode, the bulk of the catalyst will be retained in the bed. Any catalyst fines not being held in the packed bed can be removed by conventional settling or filtration.

Once catalyst solids are separated from the liquid, the liquid product may be used directly. In many cases, the content of the resulting alkanes from the reaction of chlorocarbons with hydrogen-containing silanes is very low and a particular use for the purified alkylsilanes may not necessitate isolation and separation of the alkanes from the alkylsilanes. However, where quality requirements dictate that the alkanes be removed, the process can further comprise separating the alkylsilanes from the alkanes. A preferred means for separating the alkylsilanes from the alkanes is distillation.

So that those skilled in the art may better understand and appreciate the instant invention, the following examples are presented. These examples are presented to be illustrative and are not to be construed as limiting the invention as claimed in the specifications herein.

EXAMPLE 1 (Not within the scope of the instant invention)

An apparatus was assembled that consisted of a liquid feed reservoir, a positive-displacement metering pump, and a ½-inch diameter by 8-inch stainless steel tube. The tube was fitted with a pressure-relief valve and a pressure gauge so that the liquid pumped into the tube could be held at a predetermined pressure. The temperature of the tube and its contents was controlled by immersing the tube into a constant temperature, circulating oil bath, the bath having a temperature control device. The outlet of the reaction tube was fitted so that effluent samples could be taken for analysis. Analyses were carried out using gas chromatographic techniques.

Two dimethyldichlorosilane (Me$_2$) solutions, each containing 3.5 weight percent methyldichlorosilane (MeH) and 5000 ppm, on a weight basis, tetramethylsilanes (Me$_4$) were prepared. These mixtures are designated Samples A and B, respectively. Sample A also contained 2500 ppm 1-chloropentane. Sample B also contained 2500 ppm 2-chloropentane. Both mixtures were fed separately as liquids to the empty tube. The temperature within the tube was maintained at 80° C. and pressure was controlled at about 40 pounds per square inch, gauge (psig) to maintain the mixtures as liquids. Feed rates were controlled so that the residence time of the liquids in the tube was about 5 minutes.

Samples of the reactor effluent were taken and analyzed by gas chromatography. Table 1 is a summary of the results of this study. The reactor effluent is reported as the percent conversion of the chlorocarbon and the percent conversion of the tetramethylsilane, designated as "ChloroC" and "Me$_4$", respectively.

TABLE 1

| Sample | % ChloroC | % Me$_4$ |
| --- | --- | --- |
| A | 3 | 4 |
| B | 22 | 7 |

The above results indicate that primary and secondary chlorocarbons are quite stable in the presence of a hydrogen-containing silane material in the absence of a suitable catalyst at the reaction conditions studied.

EXAMPLE 2

Using the same apparatus and procedures of Example 2, the mixture identified in Example 1 as Sample A and containing 1-chloropentane was contacted with various metal chlorides. Again reaction temperature was maintained at 80° C. and residence time within the tube was maintained at about 5 minutes. The metal chlorides evaluated were commercially available reagent grade materials. In addition, a sample of AlCl$_3$ deposited on graphite (AlCl$_3$/C) and a sample of FeCl$_3$ on silica (FeCl$_3$/SiO$_2$) were also evaluated. The AlCl$_3$/C was 35 to 40 weight percent AlCl$_3$ on graphite, purchased from Alpha Products, Morton Thiokol, Inc., Danvers, Mass. The FeCl$_3$/SiO$_2$ was FeCl$_3$ on silica gel (0.6 mmole/g reagent), purchased from Alpha Products. Samples of 11 metal chlorides and 2 samples of metal chlorides on a solid support were evaluated. These evaluations are designated as Samples C, D, E, F, G, H, J, K, L, M, N, P, and Q, respectively.

Samples of the reactor effluent were taken for each evaluation and analyzed by gas chromatography. Table 2 is a summary of the results of this study. The samples are identified by the catalyst used, designated in Table 2 as "Catalyst". The reactor effluent for each catalyst is reported as the percent conversion of the chlorocarbon to saturated hydrocarbon and the percent conversion of the tetramethylsilane, designated as "ChloroC" and "%Me$_4$Si", respectively. Sample A from Example 1 is included for comparison the effect of no catalyst.

TABLE 2

| Sample | Catalyst | % ChloroC | % Me$_4$Si |
| --- | --- | --- | --- |
| C | AlCl$_3$ | 100 | 70 |
| D | CoCl$_2$ | 100 | 84 |
| E | ZrCl$_2$ | 100 | 100 |
| F | CuCl$_2$ | 51 | 48 |
| G | FeCl$_3$/SiO$_2$ | 44 | 33 |
| H | AlCl$_3$/C | 40 | 38 |
| J | SnCl$_4$ | 26 | 33 |
| K | PdCl$_2$ | 20 | 27 |
| L | FeCl$_3$ | 20 | 34 |
| M | CaCl$_2$ | 17 | 37 |
| N | ZnCl$_2$ | 5 | 4 |
| P | NiCl$_2$ | 5 | 9 |
| Q | CrCl$_2$ | 4 | 3 |
| A | None | 3 | 4 |

The above results demonstrate many Lewis acid forming materials are effective in converting chlorocarbons essentially to saturated hydrocarbons at the above conditions.

EXAMPLE 3

An evaluation similar to that carried out in Example 2 was made with the mixture designated as Sample B in Example 1, a sample containing 2-chloropentane. Three metal chlorides were evaluated. These evaluations are designated as Samples R, S, and T, respectively.

Samples of the reactor effluent were taken for each evaluation and analyzed by gas chromatography. Table 3 is a summary of the results of this study. The notation used in Example 2 are applied to Table 3. Sample B from Example 1 is included for comparison of the effect of no catalyst.

TABLE 3

| Sample | Catalyst | % ChloroC | % Me₄Si |
|---|---|---|---|
| B | None | 22 | 7 |
| R | AlCl₃ | 99 | 100 |
| S | FeCl₃ | 79 | 51 |
| T | CuCl₂ | 78 | 48 |

The above results further demonstrate that Lewis acid forming materials are effective in converting chlorocarbons to saturated hydrocarbons at the above conditions.

EXAMPLE 4

Using apparatus, procedures, and analyses similar to those applied in Example 1, a mixture of methylchlorosilanes and minor portions of chlorocarbons and hydrocarbons was fed to a column packed with alumina pellets. The reactor was operated at a temperature of 80° C. and a pressure of 40 psig. Liquid feed to the reactor was controlled so that a residence time of about 15 minutes was maintained.

The alumina utilized was United Catalysts CS 331-4(1/16"×¼" extrudates) purchase from United Catalysts, Inc., Louisville, Ky.

Tables 4 and 5 are summaries of the methylchlorosilane and hydrocarbon/chlorocarbon content of the feed to and effluent from the reactor. Table 4 is a summary of the chlorocarbon and hydrocarbon content in and out of the reactor. The content of each component is reported in ppm based upon the total mixture and designated as "ppmin" and "ppmout". Table 5 is a summary of the methylchlorosilane content of the mixture in and out of the reactor. The content of each component is reported in weight percent and is designated as "% in" and "% out".

TABLE 4

| Component | ppmin | ppmout |
|---|---|---|
| Isopentane | 3744 | 4004 |
| 2,3-Dimethylbutane | 808 | 803 |
| Isobutane | 778 | 854 |
| 3-Methylpentane | 598 | 624 |
| n-Butane | 257 | 341 |
| n-Pentane | 101 | 163 |
| 2-Methylpentane | 50 | 29 |
| Isopropyl Chloride | 1631 | 13 |
| 2-Chloro-2-methylbutane | 61 | 0 |
| 2-Methyl-2-butene | 256 | 0 |
| Trans-2-butene | 175 | 0 |
| Cis-2-butene | 109 | 0 |
| Isobutene | 22 | 0 |

TABLE 5

| Component | % in | % out |
|---|---|---|
| Methyltrichlorosilane | 54.3 | 54.8 |
| Trimethylchlorosilane | 22.1 | 22.2 |
| Methyldichlorosilane | 16.2 | 15.7 |
| Tetramethylsilane | 2.0 | 1.9 |
| Dimethyldichlorosilane | 0.9 | 1.4 |

The above results further demonstrate that an alumina catalyst is effective in converting chlorocarbons to alkanes as well as consuming olefins.

EXAMPLE 5

A series of runs was made in a similar fashion to Example 4 in which a mixture of methylchlorosilanes and chlorocarbons and hydrocarbons was passed through a bed of alumina. A run made with no catalyst and two runs evaluating two alumina materials, Alcoa F-1 and United Catalysts T-1894. The Alcoa F-1 was purchased from Aluminum Company of America, Pittsburgh, Pa. These three runs are designated as Samples U, V, and W, respectively. The column was maintained at 80° C. and residence time of the feed in the column was about 5 minutes.

The methylchlorosilane/chlorocarbon mixture consisted of 0.25 weight percent 1-chloropentane, 0.49 weight percent Me₄, 3.6 weight percent MeH, the remainder being Me₂.

Table 6 is a summary of the results of these three runs comparing conversion of the chlorocarbon (1-chloropentane). The notation utilized in Example 3 is utilized in Table 8.

TABLE 6

| Sample | Catalyst | % ChloroC |
|---|---|---|
| U | None | 6.8 |
| V | F-1 | 93.7 |
| W | T-1894 | 99.6 |

EXAMPLE 6

A series of runs was carried out to evaluate the impact of temperature and residence time upon the reaction to convert chlorocarbons to saturated hydrocarbons. The apparatus and procedures are similar to those used in the preceding examples.

The catalyst evaluated was an alumina catalyst. United Catalysts CS-331-4, purchased from United Catalysts. The catalyst was 1/16-inch by ¼-inch extrudates.

A master batch of methylchlorosilane feed containing a chlorocarbon material was prepared. The methylchlorosilane masterbatch consisted primarily of Me₂, with 4.15 percent MeH, 2775 ppm Me₄, and 1264 ppm 2-chloro-2-methylbutane, the proportions of these components being expressed in a weight relationship in the mixture.

Nine runs were made to study the effects of temperature and residence time upon the conversion of the chlorocarbon to saturated hydrocarbons. The runs are designated Samples X, Y, Z, AA, BB, CC, DD, EE, and FF. respectively. Residence time was varied between about 1 and 8 minutes by varying the feed of the methylchlorosilane mixture to the packed reaction tube. The temperature of the reaction was varied by varying the temperature of the constant temperature bath. All runs were made at a reactor pressure of 40 pounds per square inch, gauge (psig). Samples of the reactor effluent were taken and analyzed by gas chromatography. Table 7 is a summary of the results of this study. Temperature (in °C.) and residence time (in minutes) are designated in Table 1 as "Temp" and "RT", respectively. The percent conversion of the chlorocarbon and the percent conversion of the Me₄, designated as "%ChloroC" and "%Me₄", respectively.

TABLE 7

| Sample | Temp | RT | % ChloroC | % Me₄ |
|---|---|---|---|---|
| X | 30 | 1 | 93 | 16 |
| Y | 30 | 4.5 | 99 | 29 |
| Z | 30 | 8 | 99 | 35 |
| AA | 55 | 1 | 98 | 29 |
| BB | 55 | 4.5 | 98 | 59 |
| CC | 55 | 8 | 98 | 78 |
| DD | 80 | 1 | 99 | 14 |
| EE | 80 | 4.5 | 99 | 41 |

TABLE 7-continued

| Sample | Temp | RT | % ChloroC | % Me4 |
|--------|------|----|-----------| ------|
| FF | 80 | 8 | 99 | 96 |

The above results demonstrate that the chlorocarbons in a methylchlorosilane mixture can be effectively converted to saturated hydrocarbons in the presence of a catalyst capable of forming Lewis acid sites. The above results also demonstrate that the catalyst capable of forming Lewis acid sites can also result in conversion of tetramethylsilane into other methylchlorosilanes under similar reaction conditions.

EXAMPLE 7

Apparatus, procedures, and analytical techniques similar to those used in the above examples were applied. A master batch methylchlorosilane mixture that was a 94:6 weight mixture of $Me_2$ and MeH was prepared. Four mixtures of the above methylchlorosilanes and varying amounts of 2-chloro-2-methylbutane were fed to a packed bed of alumina. These runs are designated as Samples GG, HH, KK, and LL, respectively. The packed reactor was maintained at temperature of 80° C. and a pressure of 40 psig. The feed rate of the liquid feed was controlled so as to maintain a residence time of 5 minutes in the reactor.

In all of the runs, the 2-chloro-2-methylbutane was essentially converted into saturated hydrocarbons. The product saturated hydrocarbons were analyzed to be 5 percent butanes, gO percent pentanes, and 5 percent hexanes.

Table 8 is a summary of the MeH and methyltrichlorosilane (Me) content of the reactor effluent for the varying levels of 2-chloro-2-methylbutane fed. The 2-chloro-2-methylbutane content of the feed is designated in Table 8 as "ppm Cl-C"; the methyldichlorosilane and methyltrichlorosilane content of the reactor effluent are designated as "%MeH" and "%Me", respectively.

TABLE 8

| Sample | ppm Cl—C | % MeH | % Me |
|--------|----------|-------|------|
| GG | 0 | 6.0 | 0 |
| HH | 980 | 5.9 | 0.1 |
| LL | 4,481 | 5.5 | 0.5 |
| KK | 18,469 | 3.9 | 2.1 |

The above results demonstrate that methyldichlorosilane is consumed during the conversion of the chlorocarbon to saturated hydrocarbons. These findings lend support to the proposed reaction in which the hydrogen-containing silane is the hydrogen source for the conversion of the chlorocarbon to a saturated hydrocarbon.

EXAMPLE 8

A series of runs was made to evaluate various alumina, zeolite, and siliceous materials as catalysts. Apparatus and procedures utilized in the previous examples were applied.

The methylchlorosilane/chlorocarbon mixture was a mixture of about 3.5 weight percent MeH, 2500 ppm 2-chloro-2-methylbutane, 5000 ppm $Me_4$, the remainder being $Me_2$. The catalyst bed was maintained at about 80° C. and residence time of the liquid feed was controlled at about 5 minutes.

5 alumina samples, one silica/alumina mixture, three molecular sieve (silicoaluminate) samples, one diatomaceous earth sample, and one silica gel sample were evaluated. These samples are designated Samples MM, NN, PP, QQ, RR, SS, TT, UU, VV, WW, and XX, respectively.

Table 9 is a summary of the results of these evaluations. The results summarized are the percent conversion of the chlorocarbon and the $Me_4$. The notation utilized in the preceding examples is applied in Table 9. Additionally the catalyst identification is denoted as "Catalyst".

TABLE 9

| Sample | Catalyst | % ChloroC | % Me4Si |
|--------|----------|-----------|---------|
| MM | CS-331-1 Alumina | >98 | 6 |
| NN | CS-331-5 Alumina | >98 | 5 |
| PP | CS-331-4 Alumina | >98 | 28 |
| QQ | T-374 Alumina | >98 | 40 |
| RR | gamma-Alumina | >98 | 34 |
| SS | Silica/Alumina | >98 | 33 |
| TT | LZ-Y82 Molecular Sieves | >98 | 20 |
| UU | SK 500 Molecular Sieves | 88 | 9 |
| VV | 3A Molecular Sieves | 23 | 4 |
| WW | Chromosorb W | 11 | 7 |
| XX | Silica Gel | 10 | 1 |

Samples MM, NN, PP, and QQ were alumina samples obtained from United Catalysts. Sample RR is an alumina sample obtained from Alpha Products. Sample SS is a silica/alumina material, containing 6 weight percent silica obtained from Alpha Products. Samples TT, UU, and VV are molecular sieves (zeolites) obtained from Alpha Products. Sample WW is a 45/60 mesh non-acid washed diatomaceous earth material obtained from Baxter Healthcare Corporation, Obetz, Ohio. Sample XX is a 40/60 mesh silica gel material obtained from Baxter Healthcare Corporation.

The above results demonstrate that alumina, silica-aluminas, and some zeolite materials (molecular sieves) are effective catalysts for the instant invention. Siliceous catalysts are only marginally effective as catalysts.

What is claimed is:

1. A process for purifying alkylsilanes to lower the content of chlorocarbon impurities, wherein said alkylsilanes have the formula, $$R^i{}_a SiX_{4-a}$$

wherein each $R^i$ is independently selected from hydrogen atoms and alkyl groups containing 1, 2, 3, 4, 5, or 6 carbon atoms; X is a halogen atom; and wherein a has a value of 1, 2, 3, or 4, said process comprising
(A) contacting crude alkylsilanes and a hydrogen-containing silane with a catalyst; wherein said crude alkylsilanes are a mixture which comprises as a major portion the alkylsilanes and as a minor portion the chlorocarbons; said chlorocarbons are selected from a group consisting of linear and branched alkylchlorides containing 3 or more carbon atoms and one or more chlorine atoms; said hydrogen-containing silane having the formula, $$R^{ii}{}_m H_n SiX_p,$$

wherein each $R^{ii}$ is independently selected from alkyl groups containing 1, 2, 3, 4, 5, or 6 carbon atoms; X is defined above; m has a value of 0, 1, 2, or 3; n has a value of 1 or 2; p has a value of 0, 1, 2, or 3; and the sum of (m+n+p) must equal 4;

and said catalyst is an effective Lewis acid forming material;

(B) facilitating reaction of the chlorocarbons with the hydrogen-containing silane in contact with the catalyst to convert the chlorocarbons to linear or branched alkanes;

(C) separating the catalyst from the alkylsilanes and alkanes; and (D) recovering alkylsilanes with lowered chlorocarbon content.

2. A process according to claim 1, where the process further comprises separating the alkylsilanes from the alkanes.

3. A process according to claim 1, wherein the catalyst is selected from a group consisting of alumina, silica-alumina mixtures, zeolites, aluminum chloride, cobalt chloride, ferric chloride, copper chloride, stannous chloride, palladium chloride, and zirconium chloride.

4. A process according to claim 1, wherein the hydrogen-containing silane is a minor portion of the crude alkylsilanes.

5. A process according to claim 1, wherein the hydrogen-containing silane is added to the crude alkylsilanes.

6. A process according to claim 4, wherein additional hydrogen-containing silane is added to the crude alkylsilanes.

7. A process according to claim 1, wherein the hydrogen-containing silane is present in a stoichiometric excess relative to the amount needed to convert the chlorocarbons to alkanes.

8. A process according to claim 1, wherein the chlorocarbons are present in the crude alkylsilanes at a concentration of greater than about 10 parts per million on a weight basis.

9. A process according to claim 1, wherein contact is carried out in a batch mode.

10. A process according to claim 1, wherein contact is carried out in a continuous mode.

11. A process according to claim 1, wherein contacting the crude alkylsilanes, the hydrogen-containing silane, and the catalyst and facilitating reaction of the chlorocarbons with the hydrogen-containing silanes are effected at a temperature greater than about 25° C.

12. A process according to claim 1, wherein the crude alkylsilanes, the hydrogen-containing silane, and the catalyst are in contact for greater than about one minute.

13. A process according to claim 2, wherein separating the alkylsilanes from the alkanes is facilitated by distillation to recover alkylsilanes with enhanced purity.

14. A process according to claim 1, wherein the crude alkylsilanes are methylsilanes, the hydrogen-containing silane is methyldichlorosilane and the catalyst is selected from a group consisting of aluminum chloride, cobalt chloride, zirconium chloride, alumina, and silica-alumina mixtures; the methylsilanes, the methyldichlorosilane, and the catalyst are in contact in a liquid phase in a range from about 1 to 20 minutes at a temperature in a range from about 25° to 100° C.; and methylsilanes of enhanced purity are recovered by distillation.

* * * * *